(12) United States Patent
Sierri et al.

(10) Patent No.: US 6,746,436 B1
(45) Date of Patent: Jun. 8, 2004

(54) DISPOSABLE ABSORBENT ARTICLE HAVING IMPROVED SIDE FEATURES

(75) Inventors: Giancarlo Sierri, Montesilvano (IT); Stefan Alois Wierlacher, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/868,541

(22) PCT Filed: Dec. 21, 1999

(86) PCT No.: PCT/US99/30565

§ 371 (c)(1), (2), (4) Date: Jun. 19, 2001

(87) PCT Pub. No.: WO00/40192

PCT Pub. Date: Jul. 13, 2000

(30) Foreign Application Priority Data

Dec. 30, 1998 (EP) .............................................. 98124826

(51) Int. Cl.$^7$ ................................................. A61F 13/15
(52) U.S. Cl. ............. 604/385.04; 385/604; 385/385.28; 385/385.31
(58) Field of Search ........................... 604/378, 385.01, 604/380, 379, 385.22, 385.28, 385.201, 385.31, 385.04, 385.17

(56) References Cited

U.S. PATENT DOCUMENTS

| 4,701,177 | A |   | 10/1987 | Ellis et al. |
| 5,009,653 | A | * | 4/1991 | Osborn, III .............. 604/385.1 |
| 5,197,959 | A | * | 3/1993 | Buell ...................... 604/385.1 |
| 5,221,275 | A | * | 6/1993 | Van Item .................... 604/387 |
| 5,429,630 | A | * | 7/1995 | Beal et al. ............... 604/385.1 |
| 5,558,656 | A | * | 9/1996 | Bergman ................. 604/385.1 |
| 5,650,223 | A | * | 7/1997 | Weinberger et al. .......... 442/62 |
| 6,131,736 | A | * | 10/2000 | Farris et al. ................ 206/440 |
| 6,306,123 | B1 | * | 10/2001 | Salerno et al. ........... 604/385.1 |

FOREIGN PATENT DOCUMENTS

| EP | 0 788 874 A1 | 8/1997 |
| GB | 2 284 767 A | 6/1995 |

* cited by examiner

Primary Examiner—Aaron J. Lewis
Assistant Examiner—Jacqueline F Stephens
(74) Attorney, Agent, or Firm—Roddy M. Bullock

(57) ABSTRACT

A disposable absorbent article adapted to form a tridimensional shape before use with a generally upwardly convex rear region, having a body facing surface and a garment facing surface, a longitudinal symmetry plane, a front end edge and a rear end edge, and comprising a liquid pervious topsheet, a backsheet joined to said topsheet and an absorbent core intermediate the backsheet and the topsheet. The disposable absorbent articles of the present invention are preferably applied directly to the user's body, and comprise improved side features which extend laterally and are capable of staying in close contact with the user's inner thigh area, and adjacent to that, when the disposable absorbent article is applied to the user's body.

9 Claims, 5 Drawing Sheets

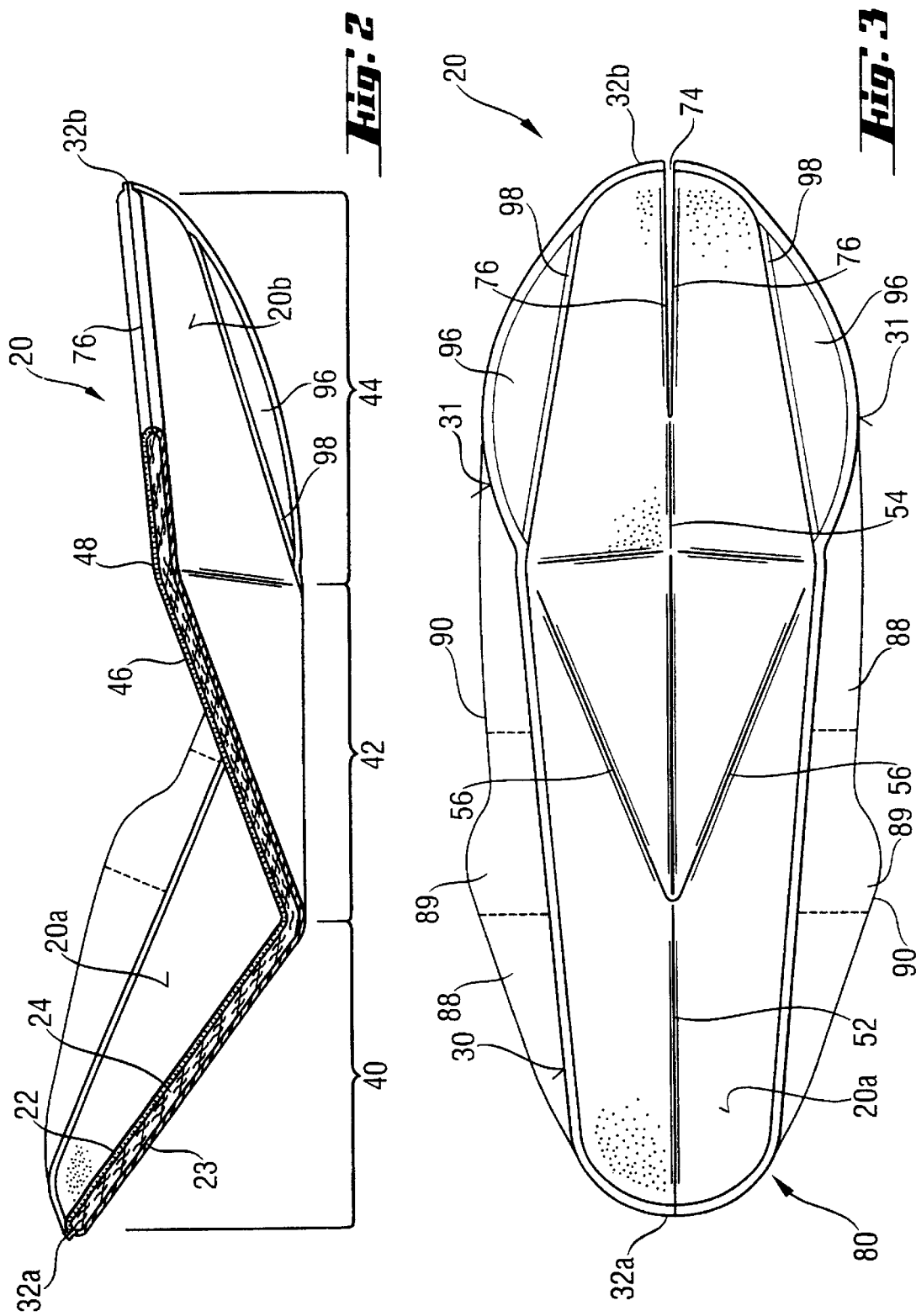

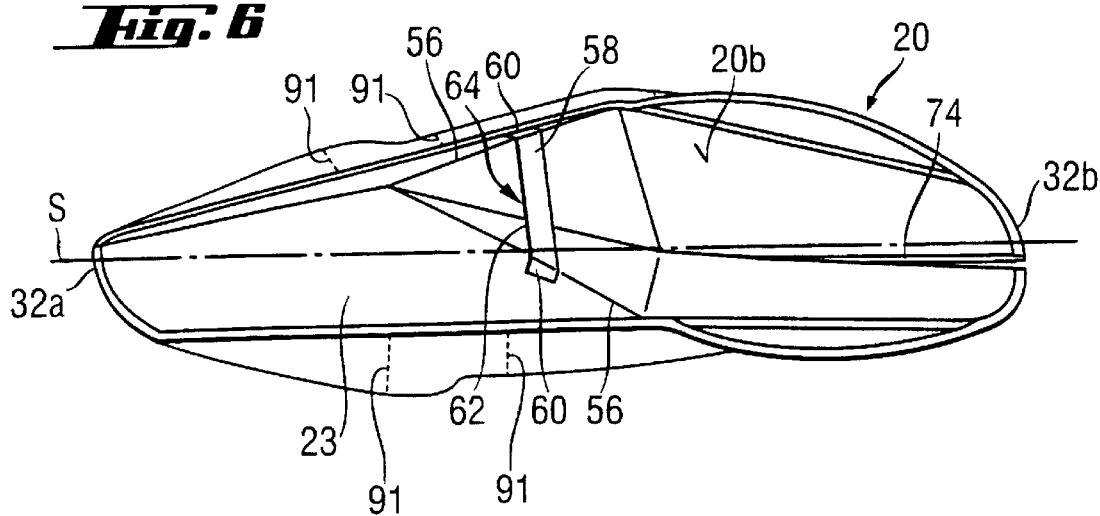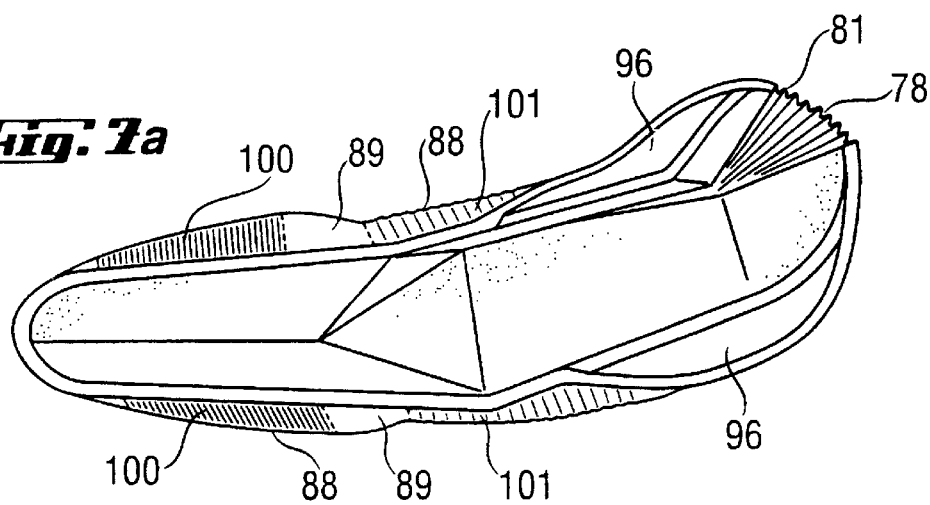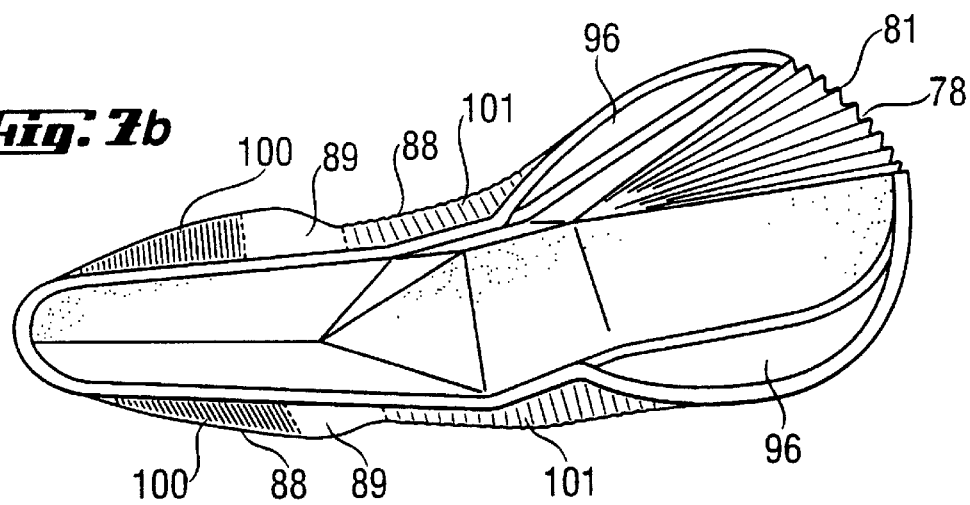

DISPOSABLE ABSORBENT ARTICLE HAVING IMPROVED SIDE FEATURES

FIELD OF THE INVENTION

The present invention relates to disposable absorbent articles. Disposable absorbent articles are considered to be absorbent devices designed to be worn externally of the body by a user and to receive fluids discharged from the body. In particular the present invention relates to disposable absorbent sanitary napkins, catamenials, incontinence inserts, and pantiliners that are adapted to form a three dimensional shape before use, in order to provide an enhanced fit for the body and reduced leakage by means of said tridimensional shape that matches the non-planar surfaces and the non-linear grooves of the body. The disposable absorbent articles of the present invention are preferably applied directly to the user's body, and comprise improved side features which extend laterally and are capable of staying in close contact with the user's inner thigh area, and adjacent to that, when the disposable absorbent article is applied to the user's body.

BACKGROUND OF THE INVENTION

In their basic form, disposable absorbent articles comprise an absorbent core interposed between a pervious body-contacting element (alternatively referred to as a topsheet or an overwrap) and an impervious protective barrier (alternatively referred to as a backsheet). The absorbent element is, of course, intended to receive and contain the fluids discharged from the body. The body-contacting element is intended to provide comfortable and dry-feeling contact with body surfaces while allowing free passage of fluids therethrough into the absorbent element. The protective barrier is intended to prevent the fluids which are expelled or which escape from the absorbent element from soiling the user's garments.

Major disadvantages of known disposable absorbent articles intended to be worn externally of the body, e.g. leakage, wet/dirty feeling, discomfort, are related to the poor body fit achieved by these articles. With respect to e.g. sanitary napkins, different attempts have been made in order to provide such articles with the capability of conforming to the body anatomy. Body conforming absorbent articles are well known in the art, both those that are initially flat, and that are adapted to form a three dimensional shape before the use in order to match the wearer's anatomy, for example by incorporating lines of preferential folding, and those that are already shaped prior to use in the desired three dimensional shape.

In European patent application No. 97122739.2 filed on Dec. 23, 1997, entitled "Tridimensional disposable absorbent article having a slit in the rear region" (P&G case CM1667Q), a tridimensional disposable absorbent article is described which has a tridimensional shape prior to use and comprises an upwardly convex rear region preferably having an inverted V shaped longitudinal ridge. The absorbent article also comprises a slit or cut in the rear region which extends from the rear end edge and is oriented substantially longitudinally. The rear cut or slit gives the preferably inverted V shaped rear portion of the absorbent article the capability of bending around an axis which is perpendicular to the symmetry plane of the article, in order to better fit the various body shapes, specifically in the area of the gluteal groove, where the rear region of the absorbent article preferably extends in order to provide a better protection.

Preferably the tridimensional disposable absorbent article can be applied directly to the user's body, rather than being applied first to the panty prior to wearing the panty itself with the attached absorbent article.

The tridimensional disposable absorbent article described in EP application No. 97122739.2 has the capability of better adjusting its shape, particularly its upwardly convex rear region, to the different anatomies taking into account the possible interactions with the undergarment, and any variations experienced during the wearing time, due e.g. to the wearer's movements, at the same time providing a better fit and a proper positioning of the rear region interested by the rear slit or cut with respect to the preferred acquisition region of the absorbent article.

Disposable absorbent articles adapted to form a three dimensional shape before the use, particularly those being already shaped prior to use such as those described in the above mentioned application, do provide a good fit to the anatomy, and therefore a better comfort to the user and a reduced leakage.

This preferred type of articles, particularly the tridimensional disposable absorbent articles described in EP 97110735.4, can be advantageously applied directly to the user's body, rather than being applied first to the panty prior to wearing the panty itself with the absorbent article attached thereon. This facilitates a good fit with the body anatomy, owing both to the preferred body conforming shape that the article can achieve, and also to the fact that a direct application to the body renders the body fitting capability of the absorbent article substantially independent of the different wearing habits and panty styles.

Side wrapping elements, or more simply side flaps or wings are a well known feature of disposable absorbent articles. Generally when absorbent articles, e.g. sanitary napkins, are provided with flaps, the flaps extend laterally from a central absorbent means and are intended to be folded around the edges of the wearer's panties in the crotch region. Commonly, the flaps are provided with an attachment means for either affixing the flaps to the underside of the wearer's panties or to the opposing flap. The flaps are particularly effective for preventing exudates from soiling the edges of the wearer's panties, owing for example to side leakage of the article in case of mispositioning, or of particularly heavy flow. Flaps also prevent portions of the panty, particularly the panty elastics in the crotch region of the undergarment, from getting at least partially between the absorbent article and the user's body, where they can contact fluid already present on the body facing surface of the absorbent article, or directly flowing from the body, therefore again leading to soiling of the undergarment.

Incorporation of side flaps in the body conforming absorbent articles mentioned above would be particularly desirable in order to increase protection of the wearer's panties against soiling in these articles which are capable of staying very close to the body due to their good fit, but problems are encountered when this preferred type of articles is intended to be applied directly to the body, before the panties are worn.

According to the usual practice with known products, the absorbent article, e.g. a sanitary napkin, is first applied to the crotch area of the panty, e.g. by means of panty fastening means such as an adhesive means, and then the flaps are caused to wrap the edges of the panty in the crotch portion, and are typically folded, and preferably also attached, to the underside of the crotch portion of the panty. Absorbent articles comprising flaps that automatically wrap the sides of a wearer's panties when the panties are pulled up, after the application of the absorbent article to the panties, are also disclosed for example in U.S. Pat. No. 5,558,663 and in U.S. Pat. No. 5,584,829. In both cases the flaps are caused to wrap the panties crotch once the article has been already applied to the panties.

In an absorbent article that is applied directly to the user's body before the panties are pulled up a correct positioning of the flaps cannot be done straightforwardly. Once the absorbent article alone is applied to the wearer's body the flaps have in fact to be kept by the user outside of the side edges of the panties in the crotch region while the panties are pulled up, in order to correctly cover said side edges and provide the desired protection against soiling. This requires attention by the user, and additional actions other than applying the article and subsequently wearing the panties, otherwise the flaps could be crumpled by the edges of the crotch area of the panties, which are also typically provided with elastic means. When the panties are pulled up and the edges move upwards along the inner part of the user's thighs, the flaps can e.g. be folded irregularly at least partially between the garment facing surface of the absorbent article and the panties themselves, therefore providing a less effective wrapping action of the panties edges and a reduced protection against soiling. In some cases the flaps cannot even prevent the side edges of the panties from getting between the absorbent article and the user's body, owing for example to a complete folding of the flaps against the garment facing surface of the absorbent article.

It is therefore an object of the present invention to provide a disposable absorbent article adapted to form a three dimensional shape before use, which is also intended to be applied directly to the user's body before an undergarment is worn, having side features capable of effectively staying over the edges of the panties in the crotch area, and of covering them to provide protection against side leakage and soiling.

It is a further object of the present invention to provide such a disposable absorbent article in which said side features are comprised in side flaps, in order to keep said side flaps in close contact, and adjacent to, the respective user's inner thigh area during panty pull up.

SUMMARY OF THE INVENTION

The present invention refers to a disposable absorbent article adapted to form a three dimensional shape before use, comprising a main body portion, a liquid pervious topsheet, a backsheet joined to said topsheet, an absorbent core intermediate the topsheet and the backsheet, a body facing surface, a garment facing surface, a longitudinal symmetry plane, and a pair of longitudinal side edges; the absorbent core has a front portion, a central portion and a rear portion, respectively corresponding to a front section, a central section, and a rear section of the main body portion, wherein at each of the longitudinal side edges at least one rider element is joined to the main body portion, wherein each of the rider elements has a bending stiffness of at least 0.02 N as defined in the Bending Stiffness Test described herein.

BRIEF DESCRIPTION OF THE DRAWINGS

While the specification concludes with claims particularly pointing out and distinctly claiming the present invention, it is believed that the present invention will be better understood from the following description in conjunction with the following drawings:

FIG. 2 is a cross-sectional view of the sanitary napkin of FIG. 1 on line 2—2;

FIG. 3 is a top view of the sanitary napkin of FIG. 1;

FIG. 6 is a perspective view of the sanitary napkin of FIG. 1, seen from the side that lies remote from the wearer in use;

FIGS. 7a and 7b are perspective views of a sanitary napkin according to the present invention similar to that illustrated in FIGS. 1 to 6, showing two in use positions of a different embodiment of the present invention.

DETAILED DESCRIPTION OF THE INVENTION

Figure 1:
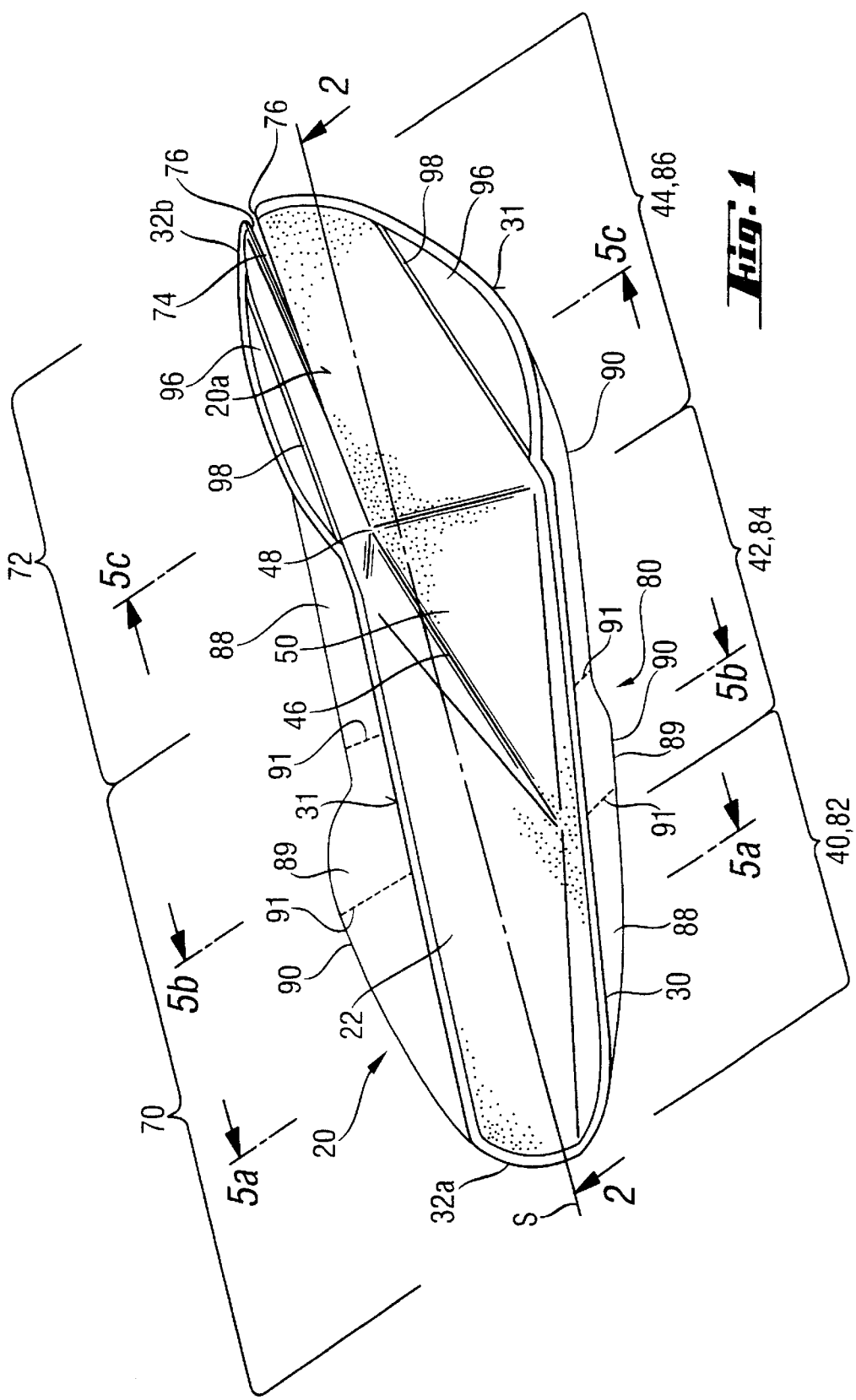
FIG. 1 is a perspective view of one embodiment of a sanitary napkin according to the present invention, seen from the side thereof that faces the wearer in use.

The present invention relates to disposable absorbent articles that are adapted to form a three dimensional shape before the use. This definition refers to articles which are already provided with a three dimensional shape prior to use, and also comprises articles which are initially flat, but incorporate features that allow the article to assume a preferred three dimensional shape before the use, e.g. being shaped by the user by means of manipulation prior to wear them. Such features can comprise e.g. preferential folding lines impressed in the article structure with known means, for example by embossment, bonding, or sealing. Such articles according to the present invention are distinct from purely flat conventional disposable absorbent articles that, when compressed and squeezed during the use, in any case assume a shape that can be said three dimensional as compared to the initial flat state, but are not adapted to form a preferred three dimensional shape before the use.

Preferably, the present invention relates to disposable absorbent articles already provided with a tridimensional shape prior to use, and more preferably having an upwardly convex, most preferably transversely inverted V shaped rear region, which exhibit absorbency for bodily fluids, the protection of the user's garments from soiling, and improved physical comfort to the user, which are also easy to produce and to package. According to a particularly preferred embodiment of the present invention that will be described hereinbelow, such articles are provided in said upwardly convex rear region with at least a cut or a slit extending from the rear end edge substantially in longitudinal direction. Said at least one cut or slit defines cut edges in the rear region of the article that are allowed to move apart in order to provide enhanced fit to the body and better conformability to the wearer's anatomy, particularly in the rear region, where the article typically extends through the posterior perineal area towards the groove between the buttocks. Such tridimensional disposable absorbent articles are preferably also provided with a tridimensional structure capable of matching the non-linear grooves and the non-planar surfaces of the female body. Unless otherwise stated, by simply saying "tridimensional absorbent article" is meant herein a disposable absorbent article adapted to form a three dimensional shape before the use, as explained above.

The tridimensional disposable absorbent articles are described below by reference to a sanitary napkin or catamenial.

The term "sanitary napkin", as used herein, refers to an article which is worn by females externally of the body and adjacent to the pudendal region and which is intended to absorb and contain the various body fluids which are discharged from the body (e.g., vaginal discharges, menses, and/or urine) and which is intended to be discarded after a single use. It should be understood, however, that the present invention is also applicable to other feminine hygiene or catamenial pads such as pantiliners, or other absorbent articles such as incontinence pads, and the like.

The term "use", as used herein, refers to the period of time that starts when the absorbent article is actually put in contact with the anatomy of the user, and of course comprises the period during which the article is worn.

The terms "joined" or "affixed", as used herein, encompasses configurations whereby a first member is directly connected to a second member and configurations whereby a first member is indirectly connected to a second member by connecting the first member to intermediate members which in turn are connected to the second member.

As used herein, the term "pudendal" refers to the externally visible female genitalia and is limited to the labia majora, the labia minora, the clitoris, and the vestibule.

According to the present invention, the tridimensional disposable absorbent article comprises at least a rider element joined to the main body portion and extending laterally from each longitudinal side edge, said rider element having a bending stiffness with respect to the main body portion such that it stays in close contact with the respective user's inner thigh area, and adjacent to it, when the disposable absorbent article is applied to the body.

FIG. 1 is a perspective view of a sanitary napkin 20 of the present invention with a preferred tridimensional structure before use, with most of the portion of the sanitary napkin 20 that faces or contacts the wearer, oriented towards the viewer. By saying "before use", it is meant that the preferred sanitary napkin 20 of the present invention is provided with a tridimensional structure before it is actually worn. The sanitary napkin can nevertheless be packaged in a folded flat configuration, being subsequently unfolded to get the tridimensional shape just before wearing it. As better shown in FIG. 2, the sanitary napkin 20 comprises a main body portion 80, a liquid pervious topsheet 22, a liquid impervious backsheet 23 joined with the topsheet 22, and an absorbent core 24 positioned between the topsheet 22 and the backsheet 23. By "main body portion" as used herein it is intended the entire absorbent article 20 excluding any side features such as the side flaps of the present invention which will be described in detail hereinafter. In the embodiment of the present invention illustrated in the enclosed drawings the main body portion 80 is the portion of the sanitary napkin 20 substantially corresponding to the overall extension of the absorbent core 24, and therefore comprises said absorbent core 24, the topsheet 22 and the backsheet 23, and is typically delimited by a peripheral seal line joining the topsheet 22 and the backsheet 23 along a periphery 30 as defined hereinafter.

The sanitary napkin 20 has two surfaces, a body facing or contacting surface 20a and a garment facing or contacting surface 20b. The body contacting surface 20a is intended to be worn adjacent to the body of the wearer while the garment surface 20b is on the opposite side and is intended to be directed towards the undergarment when the sanitary napkin 20 is worn, e.g. placed against it. Corresponding body facing and garment facing surfaces can also be identified in each single layer that constitutes the sanitary napkin 20, e.g., in the absorbent core 24. The sanitary napkin 20 has a longitudinal symmetry plane S. The term "longitudinal", as used herein, refers to a line, axis or direction in the sanitary napkin 20 that is generally aligned with (e.g., approximately parallel to) a vertical plane which bisects a standing wearer into left and right body halves when the sanitary napkin 20 is worn. The symmetry plane S of the sanitary napkin 20 substantially corresponds to this vertical plane that bisects the standing wearer. While it is preferred that the sanitary napkin 20 is exactly divided by the longitudinal symmetry plane S into two symmetrically equal halves, it is not excluded that the two halves be not specular. The term "transverse", as used herein, refers to a direction that is generally perpendicular to the longitudinal symmetry plane. The term "longitudinally oriented" refers to a direction, as seen in plan view, comprised within ±45 degrees, of the longitudinal symmetry plane S; the term "transversely oriented" similarly refers to any other direction, as seen in plan view.

The terms "front" and "rear", as used herein, refer to portions or edges in the sanitary napkin 20 that are oriented towards the front and rear part of the wearer's body, respectively, when the sanitary napkin 20 is being worn.

The main body portion 80 of the sanitary napkin 20 has a periphery 30, that is defined by the outer edges of the main body portion 80 and typically corresponds to the peripheral seal line along which the topsheet 22 and the backsheet 23 are joined together around the absorbent core 24. The periphery 30 of the main body portion 80 also comprises longitudinal side edges 31 aligned with the longitudinal symmetry plane S, and end edges comprising a front end edge 32a and a rear end edge 32b. The absorbent core 24 of the sanitary napkin has a front portion 40, a central portion 42 and a rear portion 44, respectively corresponding to a front section 82, a central section 84, and a rear section 86 in the main body portion 80, each one of said corresponding portions and sections preferably corresponding to approximately one third of the total length of the absorbent core 24. A front region 70 and a rear region 72 are identified in the sanitary napkin 20, respectively comprising at least the front portion 40 and at least the rear portion 44 of the absorbent core 24.

According to the present invention the sanitary napkin 20 further comprises at each longitudinal side edge 31 at least one rider element 89 joined to the main body portion 80 and having a bending stiffness with respect to said main body portion 80 of at least 0.02 N, as measured according to the Bending Stiffness Test described hereinafter.

In the preferred embodiment of the present invention illustrated in FIGS. 1 to 6 the sanitary napkin 20 further comprises a pair of side flaps 88, each one laterally extending outward beyond a respective longitudinal side edge 31 of the main body portion 80, to a respective distal edge 90, and joined to the main body portion 80 along said respective longitudinal side edge 31. The side flaps 88 extend along at least part of the central section 84 of the main body portion 80, but in the preferred embodiment illustrated in FIGS. 1 to 6 the side flaps 88 extend along substantially the entire front and central sections 82 and 84, and part of the rear section 86. In the preferred embodiment of the present invention illustrated in FIGS. 1 to 6 a rider element 89 is comprised in each side flap 88. Of course the periphery 30 of the main body portion 80 does not correspond to the outer periphery of the whole sanitary napkin 20 in correspondence of the side flaps 88.

In the preferred embodiment of the present invention the tridimensional sanitary napkin 20 is already provided prior to use with a tridimensional structure that is intended to match the complex body shapes of the female anatomy. The tridimensional structure has more preferably a structural tridimensionality, by "structural tridimensionality" being meant that the structure cannot be completely flattened onto a flat surface while keeping its integrity, that is, without being in any case e.g. torn, crushed or squeezed. In other words, the tridimensional structure cannot be achieved by simply folding or pleating an initially flat article, but is inherently owned by the absorbent article according to the present invention. The tridimensional sanitary napkin 20 of the present invention has preferably a substantially constant thickness, that is more preferably less than 5 mm; the sanitary napkin can be therefore considered of the thin type.

While the topsheet, the backsheet, and the absorbent core may be assembled in a variety of well known configurations (including so called "tube" products or side flap products), FIG. 1 shows a preferred embodiment of the sanitary napkin 20 in which the topsheet 22 and the backsheet 23 have length and width dimensions generally larger than those of the absorbent core 24. The topsheet 22 and the backsheet 23 extend beyond the edges of the absorbent core 24 to thereby form the periphery 30 of the main body portion 80 of the sanitary napkin 20, typically where they are joined together around the absorbent core 24 by means of a peripheral seal. The side flaps 88 can be provided as separate elements joined to the main body portion 80 along the longitudinal side edges 31. Alternatively, in the illustrated embodiments of the present invention the side flaps 88 are formed by portions of the topsheet 22 and of the backsheet 23 extending laterally further beyond the periphery 30 of the main body portion 80. In this latter case, and as illustrated in FIGS. 1 to 3, a peripheral seal joining topsheet and backsheet is preferably present around the absorbent core also in the area where the side flaps are present, running inboard of the respective distal edge 90 of the side flap, and thereby corresponding to the longitudinal side edges 31 of the main body portion 80. Other component elements of the main body portion 80 further extending laterally outward of the longitudinal side edges 31 of the main body portion 80 can be comprised in the side flaps 88, or, alternatively, the side flaps 88 can be formed by only one component element of the main body portion further extending laterally outward of the longitudinal side edges 31, e.g. the topsheet, or preferably the backsheet. In alternate embodiments this peripheral seal around the core, inboard of the distal edge 90 of the side flaps, may not be present in the area of the side flaps 88; in this case the longitudinal side edges of the main body portion in this area are meant herein to correspond to the longitudinal side edges of the absorbent core 24. The side flaps 88 are preferably liquid impervious.

The topsheet 22 is compliant, soft feeling, and non-irritating to the wearers skin. Further, the topsheet 22 is liquid pervious, permitting liquid (e.g. menses and/or urine) to readily penetrate through its thickness. A suitable topsheet 22 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibres (e.g., wood or cotton fibers), synthetic fibres (e.g., polymeric fibres such as polyester, polypropylene, or polyethylene fibres); or from a combination of natural and synthetic fibres.

A preferred topsheet comprises an apertured formed film. Apertured formed films are preferred for the topsheet because they are pervious to body fluids and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer.

Suitable formed films are described in U.S. Pat. No. 3,929,135, issued to Thompson on Dec. 30, 1975; U.S. Pat. No. 4,324,246, issued to Mullane, et al. on Apr. 13, 1982; U.S. Pat. No. 4,342,314, issued to Radel, et al. on Aug. 3, 1982; U.S. Pat. No. 4,463,045, issued to Ahr, et al. on Jul. 31, 1984; and U.S. Pat. No. 5,006,394, issued to Baird on Apr. 9, 1991. A preferred topsheet for the absorbent article of the present invention is a formed film described in one or more of the above patents and marketed on sanitary napkins by The Procter & Gamble Company of Cincinnati, Ohio as "DRI-WEAVE".

In a preferred embodiment of the present invention, the body or exposed surface of the formed film topsheet is hydrophilic so as to help liquid transfer through the topsheet faster than if the body surface were not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, Aziz et al., filed on Nov. 19, 1991, now abandoned. Alternatively, the body surface of the topsheet can be made hydrophilic by treating it with a surfactant such as is described in U.S. Pat. No. 4,950,254.

The absorbent core 24 may be any absorbent means that is capable of absorbing or retaining liquids (e.g., menses and/or urine). The absorbent core 24 may be manufactured in a wide variety of sizes and shapes (e.g., rectangular, oval, hourglass, asymmetric, etc.) and from a wide variety of liquid-absorbent materials commonly used in sanitary napkins and other absorbent articles such as comminuted wood pulp that is generally referred to as airfelt. Examples of other suitable absorbent materials include creped cellulose wadding, modified cross-linked cellulose fibres (such as those described in U.S. Patent No. 5,217,445 issued to Young, et al. on Jun. 8, 1993), capillary channel fibres (that is, fibres having intra-fibre capillary channels such as those described in U.S. Pat. No. 5,200,248 issued to Thompson, et al. on Apr. 6, 1993), absorbent foams (such as those described in U.S. Pat. No. 5,260,345, issued to DesMarais, et al. on Nov. 9, 1993 and U.S. Pat. No. 5,268,244 issued to DesMarais, et al. on Dec. 7, 1993), thermally bonded airlaid materials (such as those material described in U.S. patent application Ser. No. 08/141,156, entitled "Catamenial Absorbent Structures Having Thermally Bonded Layers For Improved Handling of Menstrual Fluids and Their Use In Catamenial Pads Having Improved Fit and Comfort" filed in the name of Richards, et al. on Oct. 21, 1993), absorbent sponges, synthetic staple fibres, polymeric fibres, hydrogel-forming polymer gelling agents, peat moss, tissue including tissue wraps and tissue laminates, or any equivalent materials or combinations of materials. Suitable absorbent cores comprising foams are described in European Applications 0 598 833, 0 598 823 and 0 598 834. Suitable absorbent cores comprising tissue laminates with particles of hydrogel-forming polymer gelling agents comprised therebetween are described in International Patent Applications WO 94/01069 and WO 95/17868.

The configuration and construction of the absorbent core may also be varied (e.g., the absorbent core may have varying caliper zones, e.g., profiled so as to be thicker in the centre), hydrophilic gradients, superabsorbent gradients, or lower density and lower average basis weight acquisition zones; or may comprise one or more layers or structures. The total absorbent capacity of the absorbent core should, however, be compatible with the design leading and the intended use of the sanitary napkin. Further, the size and absorbent capacity of the absorbent core may be varied to accommodate different uses such as incontinence pads, pantiliners, regular sanitary napkins, or overnight sanitary napkins. Preferably the absorbent articles of the present invention are sanitary napkins which are uniform in thickness.

The backsheet 23 and the topsheet 22 are positioned adjacent the garment facing surface 20b and the body facing surface 20a, respectively, of the absorbent core 24 and are preferably joined thereto and to each other by attachment means (not shown) such as those well known in the art. For example, the backsheet 23 and/or the topsheet 22 may be secured to the absorbent core 24 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

The backsheet 23 is impervious to liquids (e.g., menses and/or urine) and is preferably manufactured from a thin plastic film, although other flexible liquid impervious materials can also be used. In use, the backsheet 23 is interposed between the absorbent core 24 and the user's undergarments. The function of the backsheet 23 is to prevent exudates which may be expelled from or which inadvertently bypass the absorbent core 24 from contacting and soiling the user's undergarments. The backsheet 23 can thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm to about 0.015 †mm. Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet 23 is preferably embossed and/or matte finished to provide a more clothlike appearance. Further, the backsheet 23 may permit vapours to escape from the absorbent core 24 (i.e., it can be breathable) while still preventing exudates from passing through the backsheet 23.

As illustrated in FIGS. 1 and 2, the tridimensional sanitary napkin 20 in its preferred embodiment has before use a tridimensional structure with a longitudinal oriented ridge 50 in the central and rear portions 42, 44 of the absorbent core 24, such that the line of intersection 46 of the longitudinal symmetry plane S with the body facing surface 20a has a slope decreasing rearwardly, i.e. towards the rear end edge 32b, in the central portion 42 and in the rear portion 44 of the absorbent core 24. This can be seen more clearly in FIG. 2, where the longitudinal sectional view of the sanitary napkin 20 shows the line of intersection 46 with its decreasing slope in the central and rear portions 42, 44.

According to a preferred embodiment of the present invention illustrated in the enclosed drawings the sanitary napkin 20 further comprises a cut or slit 74 in its rear region 72, extending from the rear end edge 32b and, in the preferred embodiment illustrated in FIGS. 1 to 3, being aligned with the longitudinal symmetry plane S. The cut or slit 74 affects the whole structure of the sanitary napkin 20, i.e., in the illustrated embodiment, the topsheet 22, the absorbent core 24 and the backsheet 23, so defining corresponding cut edges 76. It is preferred that the structure of the sanitary napkin 20 is sealed along the cut edges 76, e.g. by joining together the topsheet 22 and the backsheet 23 by means of adhesive, or heat, or any other known means, so that portions of the cut absorbent core 24 are not exposed along the cut edges 76. The cut or slit 74 allows the cut edges 76 of the sanitary napkin 20 to move apart form each other along said cut or slit 74, so that the longitudinally oriented, preferably inverted V shaped structure of the ridge 50 can bend at any point along the cut or slit 74 around an axis that is perpendicular to the symmetry plane S, as better shown in FIGS. 7a and 7b, where a slightly different embodiment of the present invention is illustrated, in order to better fit the body anatomy typically in the region of the gluteal groove, where the rear region 72 of the tridimensional sanitary napkin 20 preferably extends in order to provide a better rearward protection.

More in detail, FIGS. 7a and 7b illustrate a sanitary napkin similar to that illustrated in FIGS. 1 to 3, and having a slightly different configuration for the side flaps 88, in two different embodiments of the rear region 72, corresponding to two different wearing situations, where the longitudinally oriented, inverted V shaped structure of the ridge 50 bends at two different points around an axis perpendicular to the symmetry plane S. This can be due to the adaptation of the article to different anatomies, i.e. to wearers having different body shape in the region of the gluteal groove, e.g., FIG. 7b could show the configuration of a sanitary napkin 20 while worn by a smaller wearer. Or, alternatively, this can be caused by e.g. different forces acting on the sanitary napkin during the use.

The cut or slit 74 therefore provides the structure of the inverted V shaped ridge 50, which would be per se less capable of bending around an axis perpendicular to the symmetry plane S without creasing and/or bending away form the body, and/or exerting a force on the remaining portions of the sanitary napkin 20 extending forward of said rear region 72, with the capability of adapting to the various body shapes, particularly in the region of the gluteal groove, therefore adjusting to different groove lengths and radii of curvature, and also to changes that typically occur with time in the same wearer, e.g. through movements.

In the preferred embodiment of the present invention illustrated in FIGS. 1 to 7, the line of intersection 46 has a preferred profile with a rearwardly decreasing slope as seen in cross-sectional view, as will be explained more in detail below.

The decreasing slope of said line of intersection 46 can be expressed mathematically if said line of intersection 46 is considered in a Cartesian x-y system lying in the symmetry plane S, wherein the x-axis is defined by the two points of intersection of the longitudinal symmetry plane S with the front end edge 32a and the rear end edge 32b of the sanitary napkin 20, substantially corresponding to the points indicated by numerals 32a and 32b in the cross-section view of the sanitary napkin 20 illustrated in FIG. 2, and wherein the body facing surface 20a faces towards positive y values.

With respect to this system of axes one can form the first derivative of the line of intersection 46. According to the present invention, the first derivative of this line 46 in the longitudinal direction has at least one value that is larger in the central portion 42 of the absorbent core 24 than at least one value in the rear portion 44 of the absorbent core 24. This includes the preferred case, illustrated in FIGS. 1 and 2, where the intersection line 46 is always inclined upward towards the rear end edge 32b with two different slopes in the central portion 42 and in the rear portion 44, and also alternative embodiments in which, e.g., the line of intersection 46 is inclined upward in the central portion 42 and downward in the rear portion 44.

The consecutive values of the first derivative of the line of intersection 46 can decrease continuously towards the rear end edge 32b, implying that the line of intersection 46 has a curved profile with a continuously decreasing slope, or, alternatively, the first derivative can assume different discrete values along the length of the intersection line 46. For example, it can be constant in either the central portion 42, or in the rear portion 44, or in both, the latter being the case of the embodiment illustrated in FIGS. 1 and 2, where the intersection line 46 is formed by two substantially rectilinear portions having constant slopes, with a slope change at a point 48 of the line of intersection 46 positioned where the central portion 42 of the absorbent core 24 merges the rear portion 44.

In the preferred embodiment of the present invention herein described the sanitary napkin 20 features a line of intersection 46 with the preferred profile, that is kept with any possible bent configuration of the rear portion 72 since the cut or slit 74 does not extend up to the point 48 where the slope change in the line of intersection 46 occurs. In other words, even if the cut edges 76 of the rear region 72 of the sanitary napkin 20 are caused to move apart along the entire length of the cut or slit 74, the longitudinal oriented ridge 50 still comprises a line of intersection 46 with the preferred slope decreasing rearwardly. In this preferred embodiment the sanitary napkin 20 therefore keeps its preferred structural tridimensionality wherever the bending axis perpendicular to the symmetry plane S is located along the cut or slit 74 in the rear region 72.

A line of intersection 46 with the above described profile in combination with the cut or slit 74 in the rear region 72 provides the preferred sanitary napkin 20 of the present invention with a longitudinally oriented ridge 50 in the central and rear portions 42, 44 of the absorbent core 24. The ridge 50 has a longitudinal non linear profile that is intended to match in use the central non linear groove of the female anatomy extending from the labia majora to the perineum and into the gluteal groove, and having approximately the shape schematically indicated in the corresponding central and rear portions 42', 44' of the curve G, also featuring a corresponding front portion 40', illustrated in FIG. 4, where the matching profile of a line of intersection 46 in a sanitary napkin illustrated in FIGS. 1 to 3 is also shown. The cut or slit 74 in the rear region 72 also provides the longitudinally oriented ridge 50 with the capability of bending around an axis perpendicular to the symmetry plane S and positioned at any location along the cut or slit 74 itself, in order to better fit the different body anatomies and the varying in use conditions in the region of the gluteal groove.

Figure 4:
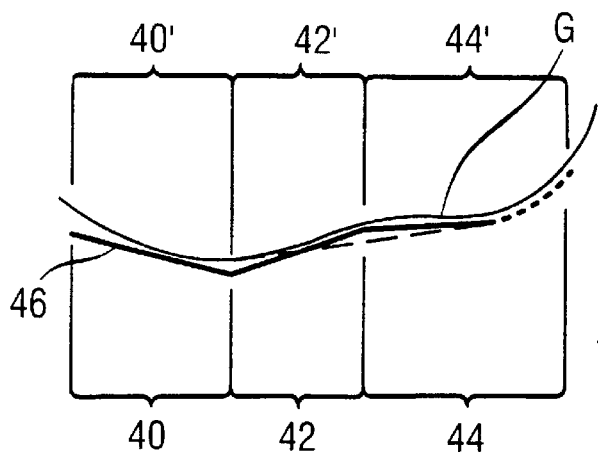
FIG. 4 is a curve taken from an anatomical section of the body of a wearer, which schematically represents the central non linear groove of the female anatomy as seen in lateral direction.

The dotted line following the rearward portion of the profile of the line of intersection 46 in FIG. 4 corresponds to the portion of the rear cut or slit 74 where the cut edges 76 are actually displaced from each other during the use of the sanitary napkin 20 of the present invention. Such dotted line does not correspond to an intersection line since, as already explained, there can be no intersection between the symmetry plane S and the body facing surface 20a where the cut edges are caused to move apart. It rather indicates the actual profile described by one of the cut edges 76 in the rear region 72 of the sanitary napkin 20 as seen in cross-sectional view, where the upwardly convex, inverted V shaped rear region of the sanitary napkin 20 is allowed to bend along an axis perpendicular to the symmetry plane S in order to better fit the body anatomy in the region of the gluteal groove, corresponding to the rearmost part of the rear portion 44' of the curve G. The profile shown in FIG. 4 can be considered as substantially corresponding to a sanitary napkin having the configuration illustrated in FIG. 7a, with the bending axis perpendicular to the symmetry plane S located closer to the rear end edge 32b.

The profile of the longitudinally oriented ridge 50 as defined by the line of intersection 46 with its slope decreasing rearwardly, and in combination with the cut or slit 74 in the rear region 72 can provide the sanitary napkin 20 with an improved fit to the wearer's body. In the preferred embodiment illustrated in FIG. 1, when going from front to rear, the forward portion of the ridge 50, with a substantially constant slope, is intended to fit the groove between the labia majora. The subsequent portion of the ridge 50 that bridges the central and the rear portions 42, 44 of the absorbent core 24, with its change in slope, has a profile that is capable of matching in use the downwardly concave portion of the central non linear groove of the female anatomy in the region going from the rearward part of the labia majora to the perineum, so as to achieve a continuous contact with the body. This provides for a better comfort and for a more effective interception of the fluids as they are released from the body. The rearward portion of the longitudinally oriented ridge 50, still belonging to the rear portion 44 of the absorbent core 24 and having a constant slope in the embodiment of FIG. 1, is intended to extend between the buttocks in the gluteal groove. Owing to its slighter slope, as compared to the forward portion of the ridge, it is capable of contacting the body without causing any stress between the anatomy and this portion of the sanitary napkin, which could in turn cause discomfort, and/or prevent the desired substantially continuous contact between the ridge 50 and the wearer's anatomy along the entire length of the non linear groove extending from the labia majora up to the gluteal groove. Finally, the rearmost portion of the ridge 50, preferably characterized by the presence of the cut or slit 74, can bend, typically upwardly, around an axis perpendicular to the symmetry plane S, in order to better fit the body shape in the area of the gluteal groove, where the rear region 72 of the sanitary napkin 20 preferably extends to provide an increased protection, e.g. against rear leakage that can be experienced during motion or during the sleep, when the wearer lies on her back. This provides for an improved fit of the sanitary napkin 20 in the area of the gluteal groove, also avoiding any possible negative interaction with the undergarment, that could otherwise exert a force on the upwardly convex rear region of the sanitary napkin 20 extending rearwardly, therefore causing said upwardly convex region to crease or move away from the body.

A ridge 50 with a preferred profile having a slope decreasing rearwardly can get further into the non linear groove of the female anatomy, as schematically indicated in FIG. 4. The ridge 50 with the profile indicated by the line 46 is in fact capable of following the profile of the groove, indicated by the curve G, by extending past a line, indicated with the dashed line in FIG. 4, that connects two points along the central groove of the body surface where the sanitary napkin has contact with the anatomy, e.g. the two points where the sanitary napkin contacts the body in correspondence of the forward and rearward portions of the ridge. The rear end of the dashed line actually goes up to the rearmost portion of the ridge 50 where the cut edges 76 are displaced form each other; it therefore corresponds to the beginning of the dotted line, as explained hereinbefore, following the profile of the line of intersection 46. A ridge shaped with a linear profile as those known in the art cannot extend past this line, since such a ridge substantially corresponds to this line, and hence cannot provide a continuous contact with the body along the entire length of the ridge.

Of course the situation described so far of a preferred tridimensional sanitary napkin 20 and its interaction with the wearer's anatomy represents only a particular preferred embodiment of the present invention, that is intended to indicate the general capability of the ridge 50 with the preferred longitudinal non linear profile, preferably in combination with the rear cut or slit 74, to match in use along its entire length the central non linear groove of the female anatomy, therefore providing for a better contact with the body and an increased comfort.

In the preferred embodiment of the present invention illustrated in FIGS. 1 and 2 the tridimensional sanitary napkin 20 preferably has a low constant thickness that is less than 5 mm, wherein the tridimensional structure is provided without the use of humps or of regions of different thickness, and it is an inherent feature of the sanitary napkin 20, rather than an added feature, achieved e.g. by bending, folding or joining together an initially planar structure.

As shown in the embodiment of the present invention illustrated in FIGS. 1 and 2, the front portion 40 of the absorbent core 24 is preferably upwardly concave, in order to better conform to the wearer's anatomy in the region of the mons pubis.

The sanitary napkin 20 illustrated in FIGS. 1 and 2 shows a particularly preferred configuration for the front, central and rear portions 40, 42, and 44 of the absorbent core 24. As viewed in transverse section the front, central and rear portions of the absorbent core 24 have respectively a V shape, a W shape, and an inverted V shape, as better shown in FIGS. 5a, 5b, and 5c, where transverse sections of the sanitary napkin 20 taken on lines 5a—5a, 5b—5b, and 5c—5c respectively of FIG. 1 are illustrated.

These different shapes provide the sanitary napkin 20 with the further capability of conforming to the wearer's anatomy in a direction substantially perpendicular to the already defined symmetry plane S. The V shape of the front portion 40 and the inverted V shape of the rear portion 44 merge together gradually in the central portion 42, where the resulting W shape is predisposed to fit the area of the labia majora and of the perineum. In use, the longitudinally oriented ridge 50 is intended to fit the longitudinal central groove as above described, while the side portions 51 bent upwardly can match the groin creases, i.e. the two grooves that are formed between the body and the legs, typically in the area where the panty elastics contact the body.

In the preferred embodiment of the present invention illustrated in FIGS. 1 and 2 the sanitary napkin 20 is provided with an increased capability of conforming to the wearer's anatomy than that simply given by the known differentiated transverse shaping of the different portions of the absorbent core 24.

The tridimensional structure of the sanitary napkin 20 prior to use is such that the width of the angle y of the inverted V shaped portion increases towards the rear end edge 32b of the sanitary napkin 20 starting from a minimum preferred value at a position corresponding to the merging of the rear portion 44 with the central portion 42 of the absorbent core 24, where it substantially corresponds to the angle β of the central inverted V part of the W shaped central portion 42, which is in turn substantially constant along the entire length of this portion 42. Therefore the rearward portion of the ridge 50, typically positioned in use between the buttocks, can more easily widen its inverted V shape during the wearing of the product without being restrained, so providing the sanitary napkin with a better conformability to the anatomical configuration of the wearer. Of course the further preferred feature of the cut or slit 74 in the rear region 72 of the sanitary napkin 20, not shown in FIG. 5c, which is a section taken at a location where the cut or slit 72 is not present, allows the cut edges 76 of the rearmost portion of the ridge 50 to move apart form each other to even better fit the region of the gluteal groove, so adapting to different lengths and radii of curvature of said groove.

A feature similar to that described for the rear portion 44 is preferably provided in the V shaped front portion 40 of the absorbent core 24, where the angle α of the V increases its width towards the front end edge 32a of the sanitary napkin 20 from a minimum preferred value at a point corresponding to the merging of the front portion 40 with the central portion 42. This will allow the portion of the sanitary napkin 20 which is closer to the front end edge 32a to more easily flatten in transverse direction during wearing in order to accommodate the relatively flat front part of the mons pubis, while still providing an overall concave shape to effectively follow the surface of the mons pubis.

The angles of the V shaped front portion 40 and/or of the inverted V shaped rear portion 44 of the absorbent core 24, and consequently of the entire sanitary napkin 20, can therefore increase towards respective end edges 32a and/or 32b up to values around 180°, in order to better accommodate the anatomy of the wearer without inducing any substantial stress in the structure, thus providing for a better fit and comfort.

The preferred feature of the angles increasing towards respective end edges in the V shaped and inverted V shaped portions is achieved by giving the front portion 40 and/or the rear portion 44 of the absorbent core 24 a cup shaped structure with any means known to the man skilled in the art. For example, in the sanitary napkin 20 of the present invention illustrated in FIGS. 1 and 2 this is achieved by cutting away a narrow V shaped portion of material centered along the longitudinal centreline of initially flat front portion 40 and rear portion 44 of the absorbent core 24, and of the topsheet 22 and the backsheet 23 as well, and having substantially the same length of the front portion 40 and of the rear portion 44, and then joining together the cut edges with known means, e.g. by thermobonding, along the junction lines identified as 52 and 54 in FIG. 3. Of course the junction line 54 does not extend up to the rear end edge 32b when the preferred cut or slit 74 has to be formed. The final tridimensional structure illustrated in FIGS. 1 and 2 is then achieved by suitably bending the non planar sanitary napkin 20, e.g. along lines of preferential bending, formed in the absorbent core 24 by means of e.g. embossments or partial cuts, such as the embossments 56 in FIG. 3, as can be readily determined by the man skilled in the art. In this preferred embodiment the cup shaped structure of the central and rear portions 42, 44 of the absorbent core 24, and therefore of the corresponding rear region 72 of the sanitary napkin 20, is intrinsically stable, i.e., has the already defined structural tridimensionality that is not hindered by the rear cut or slit 74, since it does not run the whole length of the rear portion 44 of the absorbent core 24 up to the peak 48.

The presence of the above described preferred feature in the sanitary napkin of the present invention illustrated in FIGS. 1 and 2 can be readily ascertained when folding transversely the sanitary napkin 20 in order to superimpose the front portion 40 or the rear portion 44 of the absorbent core over the central portion 42 along a fold line that approximately in the unfolded sanitary napkin corresponds to a line separating respectively the front portion 40 or the rear portion 44 from the central portion 42: in both cases the folding line will show an angle rather than being rectilinear.

The combination of the tridimensional structure of the sanitary napkin 20 of the present invention, comprising the longitudinally oriented ridge 50 with the preferred profile of the line of intersection 46, with the preferred rear cut or slit 74 in the rear region 72, provides the sanitary napkin 20 with an increased capability to fit to the non-planar surfaces and the non-linear grooves of the female anatomy, along the entire length of the sanitary napkin. The improved fit achieved by a tridimensional sanitary napkin, particularly a tridimensional sanitary napkin in the preferred embodiment described so far, is capable of providing a proper and stable positioning of the sanitary napkin during the use. There is therefore no risk that the sanitary napkin is mispositioned with respect to the anatomy, or is moved from its preferred location during the use. This provides that in use the liquid is properly received and acquired in an acquisition zone preferably located in the central portion 42 of the absorbent core 24, typically forward of the peak 48 of the ridge 50, while the rear region of the sanitary napkin preferably characterized by the slit or cut is positioned rearwardly of this acquisition zone. The cut or slit 74, in turn, being oriented substantially longitudinally, does not create any obstacle to the diffusion of the liquid within the absorbent core 24, which itself occurs in a preferred path oriented in longitudinal direction.

The rear cut or slit 74 can therefore be left completely open, with no need of an additional material joining the cut edges 76.

In an alternative preferred embodiment of the present invention, however, illustrated in FIGS. 7a and 7b, the sanitary napkin 20 can comprise a material 78 that joins the cut edges 76 of the rear cut or slit 74, and that allows the cut edges 76 to move apart. Said material 78 is preferably liquid impervious, therefore providing the article with an added protection in the rear region 72 with the cut or slit 74. Said material 78 shall be provided by any known means with the capability of allowing the cut edges 76 to move apart, e.g. it can be extensible, elastic, or pleated, as illustrated in FIGS. 7a and 7b, where a liquid impervious plastic film 78 provided with pleats 81 and joining the cut edges 76 along their entire length is shown. The material 78 can be a separate element added to the structure of the sanitary napkin 20, e.g. joined to the backsheet 23, or can be integral with the structure, being e.g. a portion of the backsheet 23 made extensible by known means.

In the preferred embodiments of the present invention shown in FIGS. 1 to 7 the sanitary napkin 20 always comprises a single rear slit or cut 74 in its rear region 72, extending from the rear end edge 32b substantially along the longitudinal symmetry plane S. In alternative embodiments of the present invention more than one cut or slit can be provided in the rear region of a tridimensional absorbent article. In further alternative embodiments the at least one cut or slit does not necessarily run along the longitudinal symmetry plane S of the tridimensional absorbent article, provided that the at least one cut or slit extends from the rear end edge in a direction towards a point located on the longitudinal symmetry plane S.

In an alternative embodiment of the present invention a tridimensional shape similar to that illustrated in FIGS. 1 to 5c can also be achieved by comprising in a disposable absorbent article a resilient insert having the desired shape, e.g. between the backsheet and the absorbent core. The insert can be comprised for example only in the central and rear portions of the absorbent article, where the ridge with the desired profile is to be provided, or can extend along the entire length of the absorbent article, in order to provide its whole shape. The resilient insert can be made of any known suitable material, e.g. absorbent or non absorbent material, and can be produced e.g. by thermoforming to get the desired tridimensional shape, preferably with a constant thickness. The insert can completely provide the tridimensional structure, or can alternatively contribute to create and to maintain said structure in an already shaped absorbent article. The insert can also comprise the cut or slit.

According to the present invention, the sanitary napkin 20 further comprises at least one rider element 89 at each longitudinal side edge 31, joined to the main body portion 80. In the preferred embodiment of the present invention illustrated in the enclosed figures the sanitary napkin also comprises a side flap 88 along each longitudinal side edge 31 of the main body portion 80, wherein each side flap 88 comprises one rider element 89. Side flaps 88 shall extend along the respective longitudinal side edge 31 in at least part of the central section 84 of the main body portion 80. In the preferred embodiment of the present invention illustrated in FIGS. 1 to 3 the side flaps 88 actually extend from along substantially the whole front section 82 to part of the rear section 86. Each rider element 89 is joined to the main body portion 50 and has a bending stiffness with respect to the main body portion 80 of at least 0.02 N as defined in the Bending Stiffness Test described hereinafter. Preferably, the bending stiffness of the rider element 89 is comprised between 0.042 N and 0.25 N, more preferably between 0.07 N and 0.15 N. The Bending Stiffness Test measures the force necessary to bend downwards the rider element 89 with respect to the main body portion 80, substantially around the longitudinal side edge 31. Of course, and as better explained in the description of the test method, the bending stiffness of a rider element 89 comprised in a side flap 88, which constitutes a preferred embodiment of the present invention illustrated in the attached drawings, will also comprise a contribution provided by the side flap itself.

In the preferred embodiment illustrated in FIGS. 1 to 3 each side flap 88 comprising the rider element 89 is constituted by portions of the topsheet 22 and of the backsheet 23 which further extend laterally outward beyond the longitudinal side edges 31 of the main body portion, but alternatively, side flaps 88 can also be separate components joined to the main body portion 80. The laterally extending portions of the topsheet 22 and backsheet 23 in turn comprise the rider element 89 therebetween. Each rider element 89, in the preferred embodiment illustrated in the enclosed drawings, extends from about half of the central section 84, to part of the front section 82. In FIGS. 1 to 3 the position of the rider elements 89 comprised between the topsheet 22 and the backsheet 23 forming the side flaps 88 is indicated by the dotted lines 91. In the illustrated embodiment the rider elements 89, the topsheet 22, and the backsheet 23 forming the side flaps 88 extend laterally up to a common distal edge 90, but other embodiments are also possible, e.g. with the rider element 89 having a distal edge inboard or outboard of the distal edge of the side flap 88. The rider element 89, as better illustrated in the section view of FIG. 5*b*, is joined to the absorbent core 24 along e.g. a junction line 94 by means of known means, e.g. adhesive or heat sealing, and also to the topsheet 22 and to the backsheet 23.

In a similar embodiment, each side flap can also be provided in e.g. two separate sections longitudinally positioned forward and rearward of the respective rider element 89, and joined to it along seal lines corresponding e.g. to the dotted lines 91 of FIG. 1. Other equivalent solutions are also possible.

In the preferred embodiment of the present invention illustrated in FIGS. 1 to 3 the absorbent core 24 has a width in transverse direction which is lower in its central portion 42, corresponding to the central section 84 of the main body portion 80, as compared to the rear portion 44 and corresponding rear section 86. The overall width of the absorbent core 24 in its three dimensional shape before the use, particularly in the preferred embodiment of the present invention where the whole absorbent article has the structural tridimensionality as defined herein, corresponds to the shortest total distance measured along the body facing surface of the core 24 between a point on the line of intersection 46 and each longitudinal side edge of the core 24, or alternatively, in the preferred embodiment of the present invention illustrated in the attached drawings, between corresponding points on each cut edge 76 and the respective longitudinal side edges in the region of the core 24 comprising the cut or slit 74. All width measurements in the absorbent article 20 of the present invention can be conducted according to this basic principle, as can be readily determined by the skilled man.

The side flaps 88 extend laterally with their respective distal edges 90 with an overall transverse width which is preferably higher than the largest width of the rear section 86 of the main body portion 80, as shown in FIG. 3. Preferably, the side flaps 88 can have a maximum width, as measured between the distal edge 90 of the side flap and the respective longitudinal side edge 31 of the main body portion 80, of from 15 mm to 50 mm, preferably of form 20 mm to 30 mm, more preferably of about 25 mm. The width of the rider elements 89 preferably correspond when possible to the width of the side flaps 88 in the absorbent article according to the preferred embodiment of the present invention, where the rider elements 89 are preferably comprised into side flaps 88.

More generally, the width of the rider elements 89, comprised in the side flaps 88 as it is preferred, or alternatively constituting the only side feature of a tridimensional disposable absorbent article according to the present invention, is to be measured between the longitudinal side edge of the absorbent core 24 and the respective distal edge of the rider element. Preferably, the width of the rider elements is comprised between 20 mm and 50 mm, more preferably between 25 mm and 40 mm.

Preferably, the width of the side flaps 88 is not constant along their length, having a maximum value preferably where the respective rider element 89 is preferably comprised. As shown in the preferred embodiment of the present invention illustrated in FIGS. 1 to 3 and 6, said width of the side flaps 88 can become narrower towards the front end edge 32*a* of the disposable absorbent article. The same drawings also show the width of the side flaps 88 gradually decreasing in the rear section 86 of the main body portion 80, where the side flaps 88 join the main body portion 80 with the absorbent core 24 having a correspondingly increasing width.

The side flaps 88 are joined to the longitudinal side edges 31 of the main body portion 80 along their entire length. By saying "joined", it is meant herein either that the side flaps 88 are constituted by separate elements actually attached or joined with known means, such as adhesive or heat sealing, to the respective longitudinal side edge 31 of the main body portion 80, or, as already explained above, that the side flaps 88 are formed by means of portions of other constituent elements of the sanitary napkin 20, e.g. preferably the backsheet 23 and the topsheet 22, that extend laterally beyond the longitudinal side edge 31 of the main body portion 80, as it is actually shown in the embodiment illustrated in FIGS. 1 to 3, and also in details in the transverse sections of FIGS. 5*a*, and 5*b*.

In the preferred embodiment of the present invention of FIGS. 1 to 6, the at least one rider element 89, which is comprised in a respective side flap 88, owing to its preferred bending stiffness with respect to the main body portion 80, which in this preferred embodiment actually corresponds to the force necessary to bend downwards the side flap 88 where it comprises the rider element 89, substantially around the longitudinal side edge 31, and as explained in detail in the Bending Stiffness Test described hereinafter, keeps the side flap 88 extending laterally outside the longitudinal edges of the main body portion of the article, in close contact with the wearer's inner thigh area, and substantially adjacent to it, when the absorbent article, having its preferred three dimensional shape before the use, is actually directly applied onto the body. Both during and after the desired positioning of the article on the body is achieved, the side flaps 88 therefore will remain in contact with the inner thigh area, and when the panties are subsequently pulled up, the side edges of the crotch portion of the panties, typically comprising elastic threads and moving upwards along the surface of the inner thighs, will neither crumple the side flaps with the rider elements nor cause them to fold improperly against the garment facing surface of the article owing to the bending stiffness induced by the rider elements. The side edges of the panties crotch will instead get correctly positioned beneath the rider elements and hence, beneath the side flaps, i.e. separate from the inner thigh by the respective side flap, typically finding their place along the longitudinal side edges 31 of the main body portion of the sanitary napkin 20. This also explains the name "rider" given to this specific element preferably incorporated into the side flaps according to the present invention. The preferred bending stiffness in fact gives the rider elements the capacity of actually "riding" the typically elasticated side edges of the panties crotch, typically when the panties are pulled up by the user, and also after they have been actually worn. The rider elements in the side flaps of the absorbent article according to the present invention moreover can also work in combination with the panties edges in the crotch area during the wearing time, since the panties edges, preferably elasticated, cooperate with the riders in the side flaps owing to the preferred bending stiffness and flexibility in order to keep the absorbent article in its right place in close contact with the body anatomy during the wearing time.

This "riding" capability of the rider elements, in terms of capacity of covering the panty crotch elastics, and of cooperating with them in use to increase body fit, is also provided in an alternative embodiment of the present invention, not shown herein, where the sanitary napkin 20 only comprises at each longitudinal side edge at least one rider element joined to the main body portion, but without side flaps. Of course the inclusion of the rider elements in a flap structure, as shown in the enclosed drawings, is preferred in order to provide a tridimensional disposable absorbent article, typically directly applied on the user's body before panty pull up, with the known benefits of side flaps, combined with the peculiar advantages of the rider elements.

The desired bending stiffness of the rider elements, preferably incorporated in the side flaps of the absorbent articles according to the preferred embodiment of the present invention, as defined in the Bending Stiffness Test described hereinafter, is determined in combination by the intrinsic flexibility characteristics of the material that constitutes the rider elements, and by the way in which the rider element is actually joined to the main body portion 80, specifically to the absorbent core 24 along e.g. the junction line 94, as shown in FIG. 5b. It corresponds in fact to a resistance opposed by the rider element 89, suitably joined to the main body portion 80, to a bending force that tries to bend the rider element 89, alone or, preferably, comprised in the side flap 88, downwardly with respect to the main body portion 80 itself, and typically around the respective longitudinal side edge 31.

According to the preferred embodiment of the present invention illustrated in the enclosed drawings one rider element 89 is comprised in each side flap 88 of the absorbent article 20, wherein each rider element 89 extends in longitudinal direction along at least part of the central section 84 of the main body portion 80, but in alternative embodiments still with rider elements comprised in side flaps each side flap can also comprise more than one rider element, for example two separate rider elements: a forward one located between the front and central section 82 and 84 of the main body portion 80, a rear one located in the rear section 86. Alternatively, multiple rider elements comprised in a side flap and forming a sort of framework are also possible. Less preferably, absorbent articles comprising only one or more rider elements along each longitudinal side edge are also possible.

In the preferred embodiment of the present invention illustrated in FIGS. 1 to 3 and 6, the side flaps 88 are constituted by portions of the topsheet 22 and of the backsheet 23 of the sanitary napkin 20, comprising therebetween the rider elements 89 as already explained. The materials for the component elements of the side flaps 88, i.e. for the topsheet 22 and the backsheet 23, are therefore those commonly used in the art for this scope, being typically soft and flexible to increase comfort.

Preferred materials for the rider elements comprise flexible, resilient materials being also soft for a better wearing comfort. In the preferred embodiment of the present invention illustrated in FIGS. 1 to 3 and 6, a suitable material for the rider elements 89 comprised in the side flaps 88 is a layer of a fluid impervious polyethylene foam having a thickness of 0.5 mm and a density of 0.2 gm/cm$^3$, such as that sold by Alveo AG of Lucerne, Switzerland, under the trade name Alveolit TEE0500.5.

In the preferred embodiment of the present invention illustrated in FIGS. 1 to 3, where, as already explained, the main body portion 80 is wider in transverse direction in its rear section 86 as compared to the central section 84, the absorbent core 24 comprises in its rear portion 44, corresponding to the rear section 86 of the main body portion, two side extensions 96. The side extensions 96 can be constituted by any suitable material, but preferably comprise the same absorbent material of the absorbent core 24, so that they can provide the core with increased absorption capacity. The side extensions 96 are joined to the core preferably by means of hinge lines 98, which allow each side extension 96 to bend along said line 98 with respect to the adjacent remaining portion of the core 24. Suitable hinge lines 98 can be provided with any known means, e.g. cuts, prefolded lines, or embossment lines. Preferably hinge lines 98 should be provided in a way that keeps the preferred absorbent side extensions 96 in fluid communication with the remaining part of the core 24. In the embodiment illustrated in FIGS. 1 to 3 the hinge lines are constituted by embossment lines, as can be more clearly seen in the sectional view of FIG. 5c.

The side extensions 96 in the rear section 86 of the main body portion 80 provide the sanitary napkin 20 with a further advantage, particularly in the illustrated preferred embodiment when a cut or slit 74 is comprised in the rear region 72. As seen in FIGS. 1 and 3 the side flaps 88 are joined to the main body portion 80 in the rear section 86 substantially to the side extensions 96 of the absorbent core 24. The possible bending movements of the side extensions 96 around the hinge lines 98 avoid that in some circumstances a tension in longitudinal direction can be directly transmitted between e.g. side flaps 88 and the rear section 86 of the main body portion 80. A longitudinal tension exerted by a side flap 88 on the respective side extension 96, due for example to body movements that act on the side flap itself, could in fact at least in part tend to pull open the cut or slit 72, with a possible reduction of the ridge height in the rearward portion of the absorbent article, and a less good fit.

However, by providing the possibility of a hinge movement between the side extensions 96 and the remaining portion of the absorbent core 24, part of this tension can be directed in a direction that does not directly pull on the sides of the cut or slit 72, for example bending the side extensions 96 slightly upwards with respect to the remaining portion of the absorbent core. This would also get a closer fit to the body in the region of the buttocks.

The side extensions 96 in the rear section 86 of the main body portion 80, particularly when they are joined to the remaining portions of the absorbent core by means of a hinge line 98, in turn also help the absorbent article to stay open and in full contact with the body, particularly in the rear section 86. This is particularly important when, as it is preferred, the absorbent article is applied directly to the body, before the undergarment is worn. During wearing of the undergarment once the absorbent article is already in its position on the body, the panty crotch finds its way more effectively within the inverted V of the rear section 86 of the main body portion 80 of the absorbent article owing to the wider rear section 86 which is kept open and in full contact with the body.

Figure 5A:
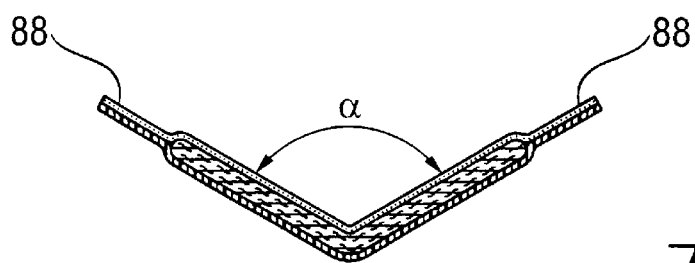
FIGS. 5a, 5b, and 5c are cross-sectional views of the sanitary napkin of FIG. 1 on lines 5a—5a, 5b—5b, and 5c—5c, respectively.
Figure 5B:
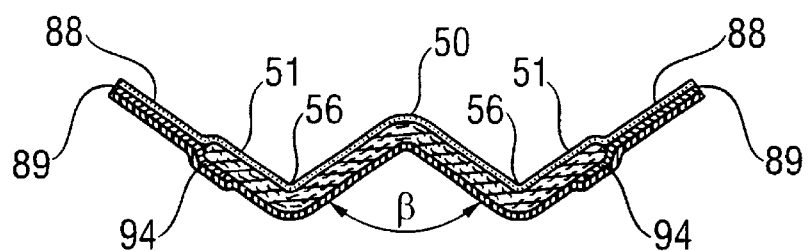
Figure 5C:
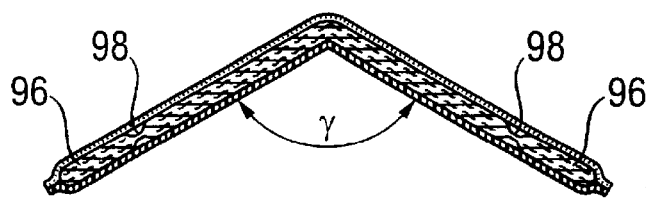

In the embodiment of the present invention illustrated in the attached drawings the rider elements 89, preferably incorporated in side flaps 88, are substantially flat, as can be seen more in detail in the sections of FIGS. 5a and 5b. However, in an alternative preferred embodiment, not illustrated, the rider elements 89 can also be bent upwardly as seen in transverse section, e.g. along a continuous curve, or alternatively comprising flat portions being angled along a bending line. This preferred bending in transverse direction contributes to keep the rider elements 89 in even closer contact with the user's inner thigh area when the absorbent article is applied to the body.

In alternative embodiments of the present invention, side flaps 88 incorporating the rider elements can also be preferably included, wherein the side flaps also comprise portions that are extensible, preferably in longitudinal direction, and/or portions that are elastically extensible, also preferably in longitudinal direction. In this context the terms "elastically extensible" and "elastic" are considered to be synonyms.

As it is known in the art, extensibility and/or elastic extensibility can be provided in selected portions of the side flaps 88 in a non limiting number of different manners. For example, the side flaps 88 can comprise a substantially inextensible material, such as the described preferred laminate comprising the topsheet 22 and the backsheet 23 further extending laterally outside of the main body portion 80. Zones of extensibility can be for example formed by ring rolling (or pre-corrugating) selected regions, as described in U.S. Pat. No. 4,107,364, U.S. Pat. No. 4,834,741, U.S. Pat. No. 5,143,679, U.S. Pat. No. 5,156,793, U.S. Pat. No. 5,167,897.

This preferred material for the side flaps 88 can also be modified such that it has a strainable network which exhibits elastic-like behaviour without added elastic material. This type of material is also referred to herein as a structural elastic-like material or "SELF" material. Suitable SELFed materials can be made according to the description in PCT applications WO 95/07675 and WO 95/20932.

In a particularly preferred embodiment of the present invention, illustrated for example in FIGS. 7a and 7b, rider elements 89 positioned and constituted as already described with reference to FIGS. 1 to 3 and 6, are preferably comprised in side flaps 88 which comprise portions 100 located longitudinally forward of the rider elements 89 which are provided with extensibility in longitudinal direction, wherein the extensibility is indicated in the drawings by means of a row of short parallel lines substantially perpendicular to the direction of extensibility, and portions 101 located longitudinally rearward of the rider elements 89 which are provided with elastic extensibility in longitudinal direction. Such elastic portions 101 are indicated in FIGS. 7a and 7b in a similar manner as the extensible portions 100, but with less closely packed parallel lines.

Portions of the side flaps which are capable of extending in longitudinal direction facilitate the bending of the side flaps with respect to the main body portion, and substantially around the longitudinal side edges 31, in the three dimensional configuration that the absorbent article has before the use. This of course occurs in combination with the bending mechanism of the rider elements already explained hereinbefore, typically during the direct application of the absorbent article to the body, before the undergarment is actually worn.

Portions of the side flaps 88 located rearward of the rider elements 89, as shown in the preferred embodiment of the present invention illustrated in FIGS. 7a and 7b, or more generally located along at least part of the central section 84 and of the rear section 86 of the main body portion 80, can be advantageously provided with elastic extensibility at least in longitudinal direction, in order to preferably behave in a similar manner as the so called "cuff elements" described in the international patent application filed by the applicant on the same date and entitled "Tridimensional disposable absorbent article having improved side features" (P&G Case CM1979FQ), within a side flap comprising rider elements according to the present invention.

According to the above mentioned application the portions 101 of the side flaps 88 provided with elastic extensibility at least in longitudinal direction are in fact in relaxed state when the absorbent article is in its preferred three dimensional shape before use, differently for example from known disposable absorbent articles comprising flaps with elasticated portions, in which the elasticated portions are applied in their stretched state to a product which is either initially flat or already curved, and in which the elasticated portions themselves keep the product in its curved shape by recovering their initially relaxed state. According to this preferred alternative embodiment of the disposable absorbent article of the present invention illustrated in FIGS. 7a and 7b, the preferred tridimensional shape formed before the use on one hand does not rely on the elasticity of the elasticated portions 101 of the side flaps 88 in order to be achieved, and on the other hand also help prevent the elasticated portions 101 of the side flaps 88 themselves from being flattened onto the surface of the absorbent article, in combination with the already explained mechanism related to the rider elements 89.

When the sanitary napkin is worn, typically by direct application on the user's body, and in combination with the already explained mechanism due to the interaction of the rider elements 89 and the user's body, the rearward portions 101 of the side flaps 88, owing to their elastic extensibility at least in longitudinal direction, will cover efficiently the body surface outside of the main body portion of the sanitary napkin 20 by being caused to follow the curvature of the sanitary napkin 20 that changes from the central section 84 to the rear section 86 of the main body portion 80. This in turn contributes to create a barrier along the longitudinal side edges 31 of the main body portion where the elasticated portions 101 of the side flaps 88 extend, to the interface between the pad and the body, particularly in the groin region where a possible movement of part of the undergarment between the absorbent article and the body is more likely to occur. In the preferred embodiment of the present invention illustrated in FIGS. 1 to 3 the cut or slit 74 extends from the rear end edge 32b substantially along the symmetry plane S. Therefore no actual line of intersection 46 can be identified where the cut edges 76 are moved apart form each other, but only where no cut or slit exists, or also where the cut edges 76 are kept close to each other and no displacement of them occurs. This is typically the case of the tridimensional sanitary napkin 20 of the present invention since the bending axis perpendicular to the symmetry plane S can move along the cut or slit 74 according to the different anatomies and/or to the changes experienced during the wearing time.

The sanitary napkin 20 of the present invention having the preferred embodiment illustrated in FIGS. 1 to 5c and described hereinbefore is typically intended to be applied by the user directly to the body, and preferably also comprises means 58 for holding and applying it located on the garment facing surface 20b and being oriented transversely, as those described in European patent application EP 97110734.7. As illustrated in FIG. 6, a perspective view of a sanitary napkin 20 similar to that of FIG. 1, and further comprising the means 58, is shown, as seen from the side that lies remote from the wearer in use, i.e., with the garment facing surface 20b towards the viewer. The means 58 for holding and applying the sanitary napkin 20 are also referred to hereinbelow as a handling aid.

Of course the means 58 for holding and applying the sanitary napkin 20 of the present invention are also intended for use by a person taking care of a user, e.g. a nurse, who handles the sanitary napkin 20 and applies it to the users body.

In the preferred embodiment of FIG. 6 the means 58 for holding and applying the sanitary napkin 20 comprises an elongated strip of elastic film material 58 oriented perpendicularly to the longitudinal symmetry plane S and located on the garment facing surface 20b of the sanitary napkin 20, in correspondence of the central portion 42 of the absorbent core 24, at a position approximately longitudinally intermediate between the front end edge 32a and the rear end edge 32b of the sanitary napkin 20. The strip 58 is affixed to the backsheet 23 at its two spaced apart ends 60 disposed on opposite sides of the symmetry plane S, with an intermediate portion 62 being not joined to said garment facing surface 20b and defining a space 64, intended for the insertion of at least one users finger for holding and applying the sanitary napkin 20. In the embodiment illustrated in FIG. 6, where the sanitary napkin 20 has the preferred tridimensional shape before use, the space 64 is actually comprised between the intermediate portion 62 of the strip 58 and the garment facing surface 20b of the central portion of the sanitary napkin, which is concave on its garment facing surface 20b, since it corresponds to the ridge 50 on the body facing surface 20a. Typically the spaced apart ends 60 of the strip 58 are fixed with known means, e.g., with an adhesive, or by thermobonding, to the garment facing surface 20b of the backsheet 23 at intermediate locations between each bend line corresponding to the embossments 56, and the respective longitudinal edge 31.

The user can put the sanitary napkin 20 on the palm of her hand with the garment facing surface 20b contacting the hand and with the front end edge 32a facing towards the wrist, at the same time inserting typically one of her fingers, e.g. the middle finger, in the space 64 between the intermediate portion 62 of the strip 58 and the backsheet 23. The user can therefore hold the sanitary napkin 20 in her open hand without exerting any force, also owing to the elasticity of the preferred material that constitutes the strip 58, with substantially the front portion of the sanitary napkin 20 lying on her palm. Application to the body can then be easily performed by the user with a single movement of her open hand, which is simple and self-explanatory as putting the empty hand on the body.

Moreover, the movements of the hand and of the fingers allow the user to completely control the manipulation of the sanitary napkin 20 during its application to the body, making use of the tactile sensitivity of the fingers to find the right position for the sanitary napkin 20. Particularly, in the preferred embodiment of the present invention, the finger inserted in the space 64 is substantially aligned with the ridge 50 on the body facing surface 20a of the sanitary napkin 20, and therefore can provide guidance to control the proper placement of the napkin 20 on the body anatomy, i.e. with the ridge 50 suitably registered with the longitudinal non-linear groove of the female anatomy extending from the labia majora to the gluteal groove. The forward portion of the ridge can be e.g. easily identified by the user with her finger inserted in the space 64, and used as a reference to direct the sanitary napkin into an optimal position on the body. The handling aid constituted by the strip 58 also allows an easy removal of the hand once the sanitary napkin 20 is in place, without disturbing or modifying the position of the napkin 20.

Since in the preferred embodiment of the present invention described so far the tridimensional sanitary napkin 20 does not comprise a panty fastening system, the handling aid of the present invention illustrated in FIG. 6 preferably also allows an easy removal and, possibly, a subsequent reapplication of the sanitary napkin 20 from the body in order to use the toilet, or to make a check of the product, or in any case in order to finally dispose of the product. The user can in fact easily grab the sanitary napkin 20 while it is being worn by positioning her hand substantially in the same way as for the application, with one of her fingers inserted in the space 64 between the not joined portion 62 of the strip 58 and the backsheet 23. The sanitary napkin 20 can therefore be taken off the body and securely held by the user; the handling aid may also be used to temporarily store the sanitary napkin, e.g. while using the toilet, on the user's hand, with no need for actually holding it with the fingers, or for exerting any force on it.

The handling aid constituted by the strip 58 allows in any event the user to handle/manipulate the sanitary napkin 20 by contacting its garment facing surface 20b only, therefore protecting her hand from the possibly dirty body facing surface 20a.

In the absorbent articles of the present invention having a tridimensional shape before the use and preferably comprising the handling aid, such as the sanitary napkin 20 in the preferred embodiment described hereinbefore, the handling aid preferably also contributes to keep the tridimensional shape of the article during the use, e.g. in case of body movements that can disturb the proper fit of the product, or when in general there is a risk of collapse of the body fitting tridimensional shape. Otherwise the handling aid, e.g. constituted by the strip 58 illustrated in FIG. 6, stays aligned or folded or loose on the garment facing surface 20b of the product and does not disturb the product performance.

In alternative embodiments of the present invention the handling aid can be constituted by more than one strip of material, or by one or more strings, while the material can be also non elastic. The handling aid can be also constituted by a strip arranged as a loop and applied to the garment facing surface 20b of the article, or by a series of loops, intended to allow the insertion of at least one user's finger.

The handling aid can also be activated by the user, e.g. by being applied to the garment facing surface of the absorbent article just before use; alternatively, a handling aid e.g. constituted by a strip 58 can be detached e.g. at one of its ends from the garment facing surface of the absorbent article and then repositioned at a different place, in order to e.g. partially control or adapt a tridimensional shape already provided in the absorbent article, or to modify the space 64 available for the insertion of at least one user's finger. A handling aid preferably constituted by a strip 58 could therefore be resealably attached to the garment facing surface 20b of the absorbent article, at either one or both ends 60, e.g. by means of a resealable adhesive, or of a mechanical fastener of the hook and loop type, such as that marketed under the tradename VELCRO. A handling aid in form of a loop could be modified by the user in order to change the diameter of the loop, and hence the space available for the insertion of the finger(s).

In a further alternative embodiment of the present invention the disposable absorbent article can comprise a release cover releasably attached to the garment facing surface of the absorbent article, wherein the handling aid is located on said release cover. In use, after application of the absorbent article to the body by means of the handling aid, the release cover can be detached from the garment facing surface of the article, leaving the adhesive exposed, that can thus serve as a panty fastening adhesive as it is already known in the art. Successive removal of the absorbent article would be performed e.g. with the known method, using the panty, with the now attached absorbent article, as an handling aid.

The handling aid does not necessarily extend across the entire width of the absorbent article, in order to define a suitable space for the insertion of at least one users finger, which is capable of achieving a sufficiently firm fit with said at least one finger.

As illustrated in the preferred embodiment of FIG. 6, the handling aid does not extend in longitudinal direction over a major portion of the length of the disposable absorbent article; preferably, it extends over less than 10% of said length, being more preferably a narrow strip with a width, extending in said longitudinal direction, of about 1 cm.

The absorbent article of the present invention can be also provided with a panty fastening means, which provides means to attach the article to the undergarment after it has been applied to the body. This would subsequently allow removal of the article from the body in a rather traditional way, i.e. by means of the panty to which the article is adhered. Panty fastening means could be located on a limited portion of the garment facing surface of the absorbent article, in order to avoid the risk of sticking to the user's hand during handling and application of the absorbent article, or, alternatively, it could be activated by the user after the absorbent article has been actually applied to the body, e.g. by removing a release paper. In any case the panty fastening means may comprise a mechanical fastener such as hook and loop fasteners such as marketed under the tradename VELCRO, snaps or holders, which would have the advantage that they do not stick to the user's hand. Alternatively, the absorbent article could be fastened to the undergarment by means of panty fastening adhesive on the backsheet 23. The panty fastening adhesive would provide a means for securing the absorbent article to the panty and preferably a means for securing the absorbent article when soiled to the fold and wrap package for convenient disposal. Any adhesive or glue used in the art for such purposes can be used for the panty fastening adhesive herein. Pressure sensitive adhesives are most preferred. Suitable adhesives include Century A-305-IV manufactured by the Century Adhesives Corporation of Columbus, Ohio, and Instant LOK 34-2823 manufactured by the National Starch and Chemical Company of Bridgewater, N.J., 3 Sigma 3153 manufactured by 3 Sigma and Fuller H-2238ZP manufactured by the H.B. Fuller Co.

The panty fastening adhesive can be typically applied to the backsheet by slot coating or spraying in various distribution patterns, such as e.g. continuous or discontinuous strips, intermittent dots, random patterns spirals.

The panty fastening adhesive should be typically covered with a removable release paper or film in order to prevent the adhesive from drying out or adhering to another surface other than the panty. Any commercially available release paper or film may be used. Suitable examples include BL 30MG-A SILOX EI/O and BL 30 MG-A SILOX 4 P/O available from Akrosil Corporation.

In a further alternative embodiment of the present invention the tridimensional disposable absorbent article can comprise a body adhesive on its body facing surface in order to be adhered directly to the wearer's body, preferably with no need of a panty fastening adhesive.

The tridimensional absorbent articles of the present invention, particularly the sanitary napkin 20, have a length that preferably ranges among the typical values commonly used for different sizes of said sanitary articles intended for substantially external disposition adjacent to the body of the wearer. Particularly, the central and rear portions 42 and 44 of the absorbent core 24 do not have preferably a length which is smaller than the total maximum length of the labia majora of an average user.

The tridimensional absorbent article of the present invention may further comprise an odour-control material for controlling unpleasant odours associated with absorbed body fluids.

Any known odour-control agent or any combination thereof that can be suitably included in a disposable absorbent article, including other materials such as binders and/or substrates, can be comprised in the absorbent article of the present invention as the odour-control material.

The odour-control material can be incorporated into the absorbent article by methods known in the art, for example layered on or into the absorbent core or mixed within the absorbent core.

In further alternate embodiments of the present invention the absorbent article can also comprise additional elements, such as an acquisition layer or a secondary topsheet positioned between the topsheet 22 and the absorbent core 24 or, alternatively, in any other suitable position.

Although the disposable absorbent article of the present invention has been described with reference to a sanitary napkin, it can be used beneficially in the context of other disposable absorbent articles such as panty liners and incontinence articles. The disposable absorbent article may thus also have all those features and parts which are typical for products in the context of their intended use.

Test Methods.

Bending Stiffness Test

Figure 8:
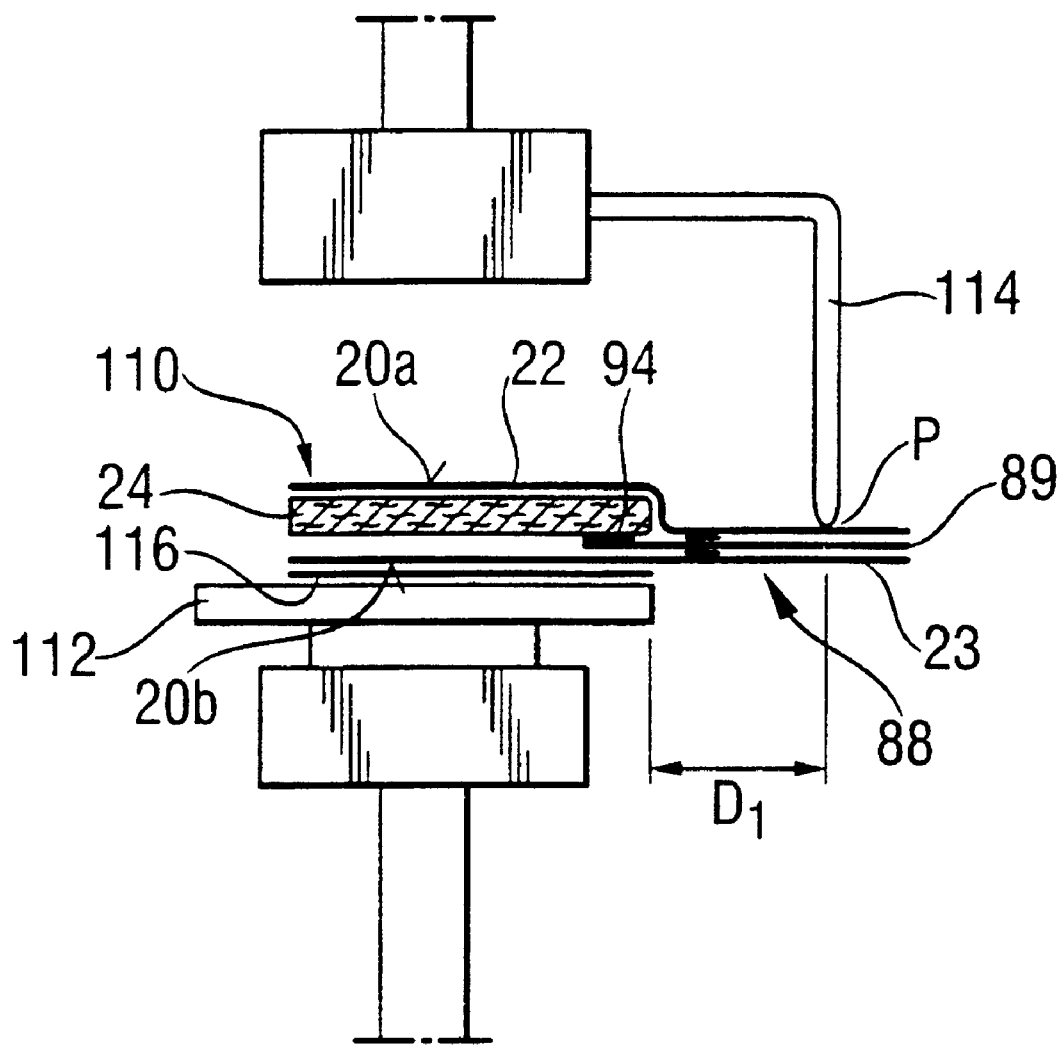
FIG. 8 illustrates an apparatus for carrying out the Bending Stiffness Test

This test method, which will be described hereinafter with reference to FIG. 8, is intended to measure the force needed to bend downward, i.e. in the direction from the body facing surface to the garment facing surface of the absorbent article, the rider element of a disposable absorbent article according to the present invention. The Bending Stiffness Test used herein is a dynamic stiffness measurement (force to deform vs. distance deformed), that determines the average force (in Newton) required to bend a rider element with respect to the main body portion of the absorbent article, substantially around the respective longitudinal side edge along which the rider element is joined to the main body portion.

Sample Preparation.

The test is performed on samples 110 prepared from the selected absorbent articles incorporating the rider elements. The absorbent article from which the samples are prepared must be new and not yet manipulated, or directly taken from the packaging in which it is provided by the manufacturer. Each sample is prepared by cutting the absorbent article with scissors along the line of intersection 46 of the longitudinal symmetry plane S with the body facing surface 20a The different elements constituting the sanitary napkin 20 are indicated in the sample 110 of FIG. 8 with corresponding reference numbers as in FIGS. 1 to 3. The transverse section of the sample indicated as 110 substantially corresponds to the right half portion of a transverse section of the absorbent article as that illustrated in FIG. 5b, wherein the sample has been flattened onto a flat surface.

Apparatus.
1) Climatically controlled Lab.
   Maintenance of 23° C. and 50% Relative humidity.
2) Instron Limited, UK Model 6021 Dynamometer.
   Interfaced to a standard IBM computer with RS232 interface for Data logging. Data are sent to the computer in the form of distance and force values, and are read into a standard Microsoft Excel worksheet for analysis. The Instron is set to run three cycles of Compression test.
Load cell=10 N
Initial clamp separation=80 mm
Final clamp separation=62 mm
Distance sample to be deformed=18 mm
Compression speed 100 mm/min 3) Scissors.
4) Plexiglas plate.
   The plexiglas plate 112 is used to hold the sample 110 in a flattened state when the test is carried on. The plexiglas plate 112 has a flat upper surface and also comprises a support, by which it can be fixed to the fixed clamp of the dynamometer with the upper surface perpendicular to the direction of motion of the moving clamp. The upper surface is larger than the sample that has to be tested and can have an approximately rectangular shape, with the longest sides substantially aligned with the length of the sample. One of the two longer sides must also have a contour that matches the contour of the longitudinal side edge of the absorbent core 24 of the sample to be tested, at least along the whole length of said longitudinal side edge of the core where the side flap of the sample comprises the rider element 89, the bending stiffness of which has to be measured.
5) Compression tool.
   The compression tool 114 is a metal cylindrical rod with a diameter of 2 mm and a rounded edge, fixed to the moving clamp by means of e.g. an L-shaped connection portion, such that it is parallel to the direction of motion of the moving clamp, as illustrated in FIG. 8.

Bending Stiffness Measurement.

The sample 110 is positioned onto the upper surface of the plexiglas plate 112 in a flattened condition, such that the longitudinal side edge of the absorbent core 24 is aligned with the matching contoured longer side of the plexiglas plate 112, and with the side flap 88 completely projecting outside of the plexiglas plate surface, as shown in FIG. 8. The sample is fixed in the flattened condition onto the upper surface of the plexiglas plate by suitable means, e.g. by means of a double sided adhesive tape 116. The fixation is achieved over the entire area of the garment facing surface 20*b* of the sample which is in contact with the upper surface of the plexiglas plate. If the absorbent article is a thin sanitary napkin according to one of the preferred embodiments of the present invention described so far and illustrated in the attached drawings, preferably characterized by the already defined "structural tridimensionality", the sample corresponding to the half portion cut along said intersection line 46 can be easily and completely flattened onto a surface without imparting substantial deformation and internal tensions to the structure. Alternatively, in case a flattened condition for the sample is not easily achieved in this way, the sample 110 can be held in a flattened condition onto the upper surface of the plexiglas plate 112 by means of a second flat plate, not illustrated, superimposed to the plexiglas plate and suitably fixed to it, and comprising the sample 110 therebetween. Other suitable means can be used in order to achieve this flattened condition for the sample, for example a smaller sample can also be prepared, by cutting from the absorbent article a portion only comprising a complete rider element and the entire portion of the main body portion where the rider element is joined. In any case, fixation of the sample 110 to the upper surface of the plexiglas plate 112 must be such that the portion of the sample directly attached to the plexiglas plate does not move with respect to the plexiglas plate during the test.

The clamps are so positioned to start the compression from a distance of 80 mm. The plexiglas plate and the compression tool are connected to the fixed clamp and to the moving clamp respectively, and they are so positioned, with respect to each other, that the edge of the compression tool only touches the body facing surface of the rider element 89 at a point P, without exerting any pressure on it. Of course, in preferred embodiments of the present invention such as those illustrated in FIGS. 1 to 6, the contact of the compression tool is actually achieved with the body facing surface of the side flap 88 where it comprises the rider element 89. In such a preferred embodiment, the bending stiffness value of the rider element evaluated according to the test method of course also comprises a contribution provided by the elements forming the side flap, e.g. the topsheet and the backsheet comprising the rider element therebetween. The distance $D_1$ measured between the point where the compression tool contacts the side flap and the longitudinal side edge of the core 24, must be of 20 mm, as shown in FIG. 8.

The position of the point P along the length of the rider element 89 is not relevant, provided the width of the rider element is thereby sufficient to allow the desired positioning of P at 20 mm from the side edge of the absorbent core. However, it is preferred that P is localised in correspondence of the largest width of the rider element.

In case the width of the rider element is not sufficient anywhere to allow the localisation of the point P at the required distance of 20 mm from the core edge, and preferably also when the largest width of the rider element is less than 35 mm, the measurement of the bending stiffness can be made on a corresponding sample having the same characteristics, but featuring a wider rider element having a largest width of 35 mm. The measurement is performed as described with the point P positioned as required in correspondence with this larger width of the rider element, and then the rider element is cut to its actual desired width.

The sample is compressed over a distance of 18 mm to a final clamp separation of 62 mm. Three compression cycles are run. The instrument details are given above.

The Instron records the clamp separation (in mm) and the force exerted to achieve this separation (in Newton) and sends this data via an RS232 interface to an IBM computer equipped with Microsoft Excel worksheet. The force and the distance data are loaded into the Excel software and the peak force measurement for each of the three 18 mm compression cycles is determined.

The bending stiffness is evaluated as the average value of the three peak values.

The measurements are performed and averaged on 5 samples of the same type to ensure a representative bending stiffness value to be determined for each sample under investigation.

The bending stiffness of a rider element of an absorbent article as described herein will be in accordance with the present invention, if at least one point P can be identified in at least one rider element, where the bending stiffness of the rider element is evaluated according to the Bending Stiffness Test method described so far has the preferred values mentioned in the description, and wherein preferably the second and the third peak values of the force do not decrease more than 20% with respect to the first peak value, in the three compression cycles of a same test.

What is claimed is:

1. A disposable absorbent article adapted to form a three dimensional shape before use, said disposable absorbent article comprising a main body portion, a liquid pervious topsheet, a backsheet joined to said topsheet, an absorbent core intermediate said topsheet and said backsheet, a body facing surface, a garment facing surface, a longitudinal symmetry plane, and a pair of longitudinal side edges, said absorbent core having a front portion, a central portion and a rear portion, respectively corresponding to a front section, a central section, and a rear section of said main body portion, said disposable absorbent article further comprising said disposable absorbent article characterized in that at each of said longitudinal side edges at least one rider element is joined to said main body portion, wherein each of said rider elements has a bending stiffness of at least 0.02 N as defined in the Bending Stiffness Test described herein.

2. A disposable absorbent article according to claim 1, characterized in that it comprises two side flaps each laterally joined to said main body portion along a respective longitudinal side edge and extending laterally outward beyond said respective longitudinal side edge of said main body portion to a respective distal edge, wherein each of said flaps comprises at least one of said riders elements.

3. A disposable absorbent article according to claim 1, characterized in that said bending stiffness is comprised between 0.04 N and 0.25 N.

4. A disposable absorbent article according to claim 1, characterized in that said main body portion is narrower in said central section than in said rear section.

5. A disposable absorbent article according to claim 4, characterized in that each of said side flaps extends from at least part of said front section to at least part of said rear section, and wherein each of said side flaps comprises one rider element extending in longitudinal direction along at least part of said central section.

6. A disposable absorbent article according to claim 1, characterized in that each of said flaps is extensible at least in longitudinal direction along at least part of its length.

7. A disposable absorbent article according to claim 1, characterized in that each of said flaps is elastically extensible at least in longitudinal direction along at least part of its length.

8. A disposable absorbent article according to claim 1, characterized in that said rider elements have a width comprised between 20 mm and 50 mm, as measured between the longitudinal side edge of said absorbent core, and a respective distal edge of said rider element.

9. A disposable absorbent article according to claim 1, characterized in that said disposable absorbent article is adapted to be applied directly to a user's body.

* * * * *